(12) United States Patent
Najafi et al.

(10) Patent No.: US 9,468,408 B2
(45) Date of Patent: Oct. 18, 2016

(54) DELIVERY SYSTEM, METHOD, AND ANCHOR FOR MEDICAL IMPLANT PLACEMENT

(71) Applicant: Integrated Sensing Systems, Inc., Ypsilanti, MI (US)

(72) Inventors: Nader Najafi, Ann Arbor, MI (US); David Joseph Goetzinger, Livonia, MI (US); Catherine Hook Morgan-Leonard, Ypsilanti, MI (US); Jacek Ryszard Baranowski, Linkoping (SE)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 39 days.

(21) Appl. No.: 14/219,332

(22) Filed: Mar. 19, 2014

(65) Prior Publication Data
US 2014/0207153 A1    Jul. 24, 2014

Related U.S. Application Data

(60) Division of application No. 13/173,076, filed on Jun. 30, 2011, now Pat. No. 8,715,300, which is a continuation-in-part of application No. 12/960,961, filed on Dec. 6, 2010, now Pat. No. 8,696,693.

(60) Provisional application No. 61/283,492, filed on Dec. 5, 2009.

(51) Int. Cl.
| | |
|---|---|
| *A61B 5/00* | (2006.01) |
| *A61B 5/0215* | (2006.01) |
| *A61F 2/24* | (2006.01) |
| *A61M 25/02* | (2006.01) |

(Continued)

(52) U.S. Cl.
CPC .......... *A61B 5/6882* (2013.01); *A61B 5/0215* (2013.01); *A61B 5/6869* (2013.01); *A61B 5/6876* (2013.01); *A61F 2/243* (2013.01); *A61F2/2493* (2013.01); *A61M 25/02* (2013.01); *A61M 39/0247* (2013.01); *A61B 5/076* (2013.01); *A61B 2560/066* (2013.01); *A61M 25/04* (2013.01)

(58) Field of Classification Search
CPC .......... A61B 2560/066; A61B 5/0215; A61B 5/076; A61B 5/6869; A61B 5/68766; A61B 5/6882; A61B 2017/00986; A61B 17/10; A61B 2017/00623; A61B 2017/1205; A61F 2/243; A61F 2/2493; A61F 2002/505; A61F 2002/9511; A61F 2/95; A61F 2002/9665; A61F 2002/011; A61M 25/04
See application file for complete search history.

(56) References Cited

U.S. PATENT DOCUMENTS 5,702,421 A * 12/1997 Schneidt ........................ 606/213
8,696,693 B2 * 4/2014 Najafi et al. .................. 606/151

(Continued)

*Primary Examiner* — Alexander Orkin
(74) *Attorney, Agent, or Firm* — Hartman Global IP Law; Gary M. Hartman; Michael D. Winter

(57) ABSTRACT

A delivery system and method for placing a medical implant, such as for diagnosing, monitoring and/or treating cardiovascular diseases. The delivery system includes a hollow catheter, an anchor coupled to the catheter, and an implant secured within the anchor. The anchor has a base portion with first and second longitudinal ends and a cage therebetween. The anchor further has flexible arms, flexible legs, features for securing the medical implant within the cage of the base portion, and a coupler portion connected to and spaced apart from the second longitudinal end of the base portion. Surfaces of the arms and legs are adapted to clamp the anchor to a wall. The system further includes a pusher wire adapted to cause the anchor to acquire a stowed configuration in which the legs axially extend from the base portion, permitting the anchor to be retrieved after its deployment.

5 Claims, 8 Drawing Sheets

(51) Int. Cl.
    *A61M 39/02*     (2006.01)
    *A61B 5/07*     (2006.01)
    *A61M 25/04*     (2006.01)

(56) References Cited

U.S. PATENT DOCUMENTS

| | | |
|---|---|---|
| 8,715,300 B2 * | 5/2014 | Najafi et al. ............ 606/142 |
| 2003/0181945 A1 * | 9/2003 | Opolski et al. ........... 606/206 |
| 2004/0116992 A1 * | 6/2004 | Wardle et al. ............ 607/116 |
| 2004/0181256 A1 * | 9/2004 | Glaser ..................... 606/213 |
| 2005/0065589 A1 * | 3/2005 | Schneider et al. ........ 607/126 |
| 2005/0148925 A1 * | 7/2005 | Rottenberg et al. ......... 604/9 |
| 2006/0009799 A1 * | 1/2006 | Kleshinski et al. ........ 606/200 |
| 2007/0088388 A1 * | 4/2007 | Opolski et al. ........... 606/213 |
| 2008/0086168 A1 * | 4/2008 | Cahill ..................... 606/213 |
| 2008/0176271 A1 * | 7/2008 | Silver et al. ............... 435/29 |
| 2010/0010511 A1 * | 1/2010 | Harris et al. ............. 606/143 |
| 2010/0030200 A1 * | 2/2010 | Strauss et al. ............... 606/1 |

* cited by examiner

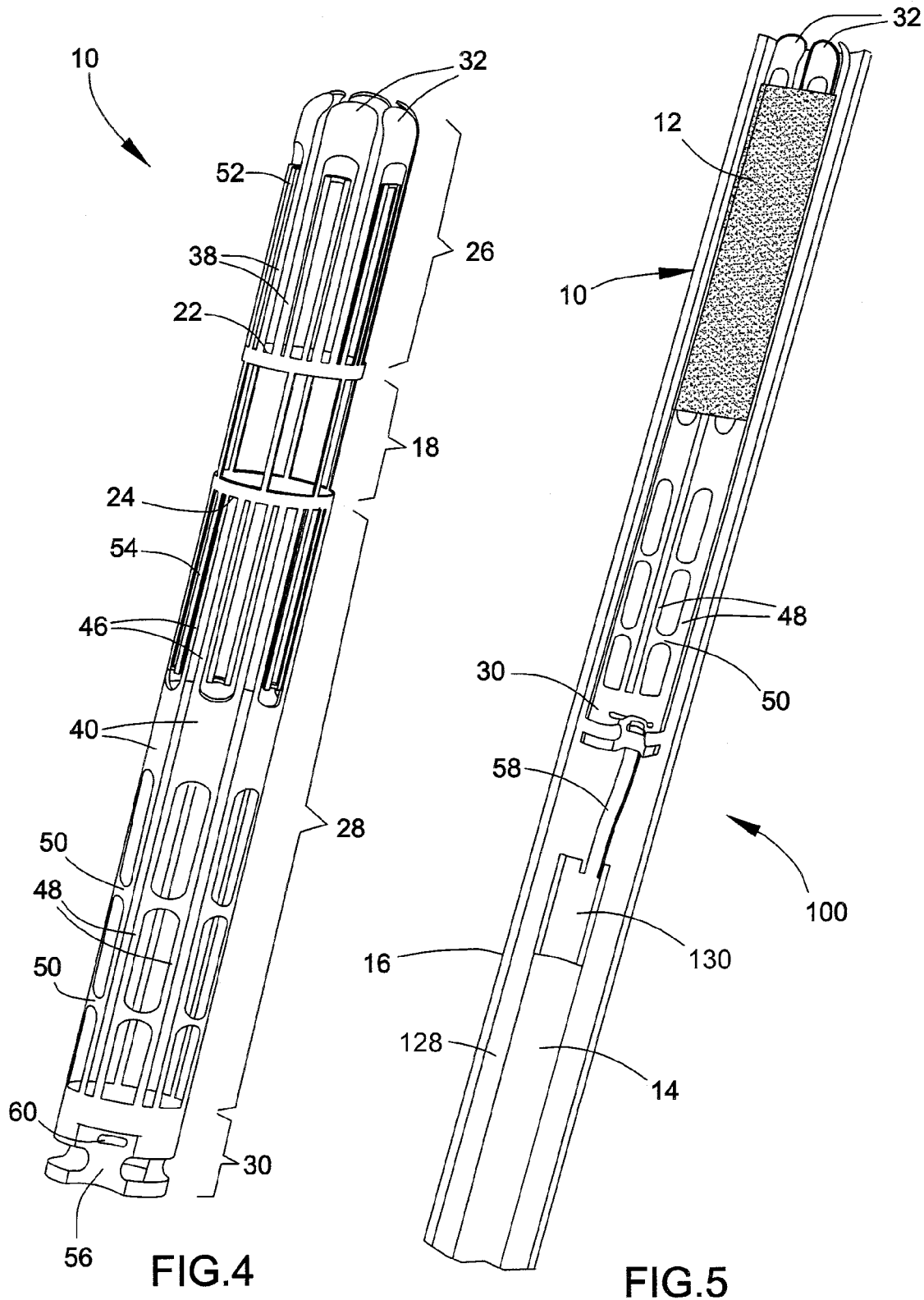

DELIVERY SYSTEM, METHOD, AND ANCHOR FOR MEDICAL IMPLANT PLACEMENT

CROSS REFERENCE TO RELATED APPLICATIONS

This is a division patent application of co-pending U.S. patent application Ser. No. 13/173,076 filed Jun. 30, 2011, which is a continuation-in-part patent application of co-pending U.S. patent application Ser. No. 12/960,961, filed Dec. 6, 2010, which claims the benefit of U.S. Provisional Application No. 61/283,492, filed Dec. 5, 2009. The contents of these patent documents are incorporated herein by reference.

BACKGROUND OF THE INVENTION

The present invention generally relates to implantable medical devices, such as of the types for monitoring physiological parameters. More particularly, the invention relates to anchors for medical implants, methods of manufacturing anchors, and methods of placing medical implants, wherein the anchors and methods are suitable for use in procedures performed to diagnose, monitor, and/or treat cardiovascular diseases, including procedures performed to monitor pressure in the left side of the heart.

Congestive heart failure (CHF), a condition in which the heart fails to pump efficiently, currently affects about 4.8 million patients (over 400,000 new patients per year in the U.S.), accounts for about 5 to 10% of all hospitalizations, and costs over $38 billion in the U.S. Following diagnosis of congestive heart failure, physicians typically monitor disease progression on a continuing basis to better tailor treatment. The best course of action for a tailored treatment involves monitoring of the pressures of the left side of the heart, particularly left ventricular end-diastolic pressure (LVEDP, also known as left ventricular filling pressure) and mean left-atrium pressure (MLAP). These pressures are recognized as the best parameters for characterizing congestive heart failure in patients. Clinical evaluation of LVEDP or MLAP is generally performed using a cardiac catheterization procedure, which provides a snapshot of pressure data a few times per year at most, carries morbidity, and is expensive. More recently, miniaturized medical implants have been developed that are adapted to be delivered with a catheter and implanted into a wall of the heart, such as the atrial septum. Once implanted, the implant is able to chronically monitor physiological parameters of the heart, for example, hemodynamic monitoring of left atrial biopressure waveforms such as LVEDP or MLAP. As such, implants of this type are well suited for diagnosing, monitoring, and/or treating cardiovascular diseases such as congestive heart failure, as well as congenital heart disease (CHD).

Monitoring pressures within the heart, and particularly pressures of the left side of the heart, is a very challenging task for many reasons, most importantly the potentially fatal outcome of any thrombi caused by the implant. Bleeding, thromboembolism and arrythmias are potentially fatal complications. Because smaller implant sizes are capable of reducing the risk for these complications, miniaturized MEMS (microelectromechanical systems) are desirable for chronic implantation. Notable examples of MEMS implants are disclosed in U.S. Pat. Nos. 6,140,144, 6,926,670, 6,968,743, 7,211,048, 7,615,010 and 7,686,762 and U.S. Published Patent Application Nos. 2006/0047205, 2007/0032734, 2008/0077016, 2008/0269573, 2009/0005656, 2009/0105557, 2009/0105784 and 2009/0143696. Pressure monitoring systems of the type disclosed in these patent references may comprise two primary components: the implant comprising an implantable telemetric pressure sensor that is batteryless or makes use of a small battery, and a companion hand-held reader. The implant further includes custom electronics for processing the output of the sensor and an antenna for telemetry and, if necessary or desired, for tele-powering the sensor. Telemetry and tele-powering can be achieved via various techniques, including but not limited to magnetic telemetry (including RF), acoustic waves, ultrasonic waves, with the currently preferred technique typically being magnetic telemetry. The reader transmits power to the sensor, and the sensed pressure is in turn transmitted back to the reader. Data collected from the sensor can then be used by a physician to tailor the treatment of the patient. Miniaturized implants of this type can provide chronic, continuous bio-pressure measurements and support the trend toward home health monitoring. In some cases, the implant may also be configured or adapted to perform additional functions, such as monitoring temperature or delivering a drug or electric signal to the muscles/nerves.

Monitoring pressures with a miniaturized implant chronically implanted within the heart is also complicated by the challenges of devising a reliable anchoring system that does not increase the risk of thrombi. Notable examples of anchors suitable for this purpose are disclosed in U.S. Pat. Nos. 7,317,951 and 7,634,319 and U.S. Published Patent Application No. 2007/0179583. Though significant advances have been achieved with these anchoring systems, further improvements are desired.

BRIEF DESCRIPTION OF THE INVENTION

The present invention provides an anchor for a medical implant, methods of manufacturing the anchor, a delivery system for the anchor and implant, and procedures for placing the anchor and implant, such as for monitoring physiological parameters. The invention is particularly directed to implantation of physiologic sensors for diagnosing and/or monitoring and/or treating cardiovascular diseases, such as congestive heart failure, valvular heart disease, systemic pulmonary hypertension, and congenital heart disease.

According to a first aspect of the invention, a delivery system is provided that includes a hollow catheter, an anchor coupled to the catheter, and an implant secured within the anchor. The anchor has a base portion having a longitudinal axis, first and second longitudinal ends in oppositely-disposed first and second longitudinal directions, respectively, of the anchor, and a cage between the first and second longitudinal ends. The anchor further has a plurality of flexible arms, a plurality of flexible legs, means for securing the medical implant within the cage of the base portion so that at least a portion of the implant is between the first and second longitudinal ends of the base portion, and a coupler portion releasably coupled to the catheter and connected to and spaced apart from the second longitudinal end of the base portion in the second longitudinal direction of the anchor. The anchor has a stowed configuration in which the arms axially extend in a distal direction from the first longitudinal end of the base portion and are resiliently biased so that, in a deployed configuration of the anchor, the arms radially project away from the first longitudinal end of the base portion and axially project toward the second longitudinal end of the base portion. Each arm has a span portion terminating in a distal portion of the arm. The distal portion has a convex surface facing the second longitudinal direction while the arm is deployed. The legs are connected to the coupler portion and to the second longitudinal end of the base portion. Each leg axially extending in a proximal direction from the second longitudinal end of the base portion in the stowed configuration of the anchor, and is resiliently biased to project radially away from the longitudinal axis of the anchor and axially project toward the first longitudinal end of the base portion in the deployed configuration of the anchor. Each leg has a first span portion adjoining the second longitudinal end of the base portion, a second span portion adjoining the coupler portion, and an intermediate portion therebetween. The intermediate portion has a convex surface facing the first longitudinal direction while the leg is deployed. When deployed within an opening in a wall, such as a septum of a heart, the convex surfaces of the distal tips and intermediate portions of the arms and legs serve to clamp the wall and thereby secure the anchor within the wall.

According to a preferred aspect of the invention, the delivery system further comprises a pusher wire received in the catheter and adapted to apply a force to the implant in the distal direction so as to cause the legs to move from the deployed configuration, whereby the legs project radially away from the longitudinal axis of the anchor and axially project toward the first longitudinal end of the base portion, to the stowed configuration, whereby the legs axially extend in the proximal direction from the second longitudinal end of the base portion.

Other aspects of the invention include methods of using the delivery system comprising the elements described above.

A technical effect of the invention is the ability to provide a reliable anchor for securing a medical implant within the human body, and a procedure for placing a variety of implantable medical devices, including those adapted to monitor physiological parameters including pressures within the heart. The anchor can be readily adapted and configured to address delivery issues, including delivery method, delivery equipment, implant design, and anchor location, that arise when employing chronically implanted physiologic devices, sensors, and actuators, particularly if used to diagnose, monitor and/or treat cardiovascular diseases such as congestive heart failure and congenital heart disease. Notably, the anchor and its delivery find application in the very challenging application of monitoring the pressure of the left side of the heart. Medical implants that can be placed and anchored in accordance with this invention can operate wirelessly or can be connected to other devices (such as pacemakers) using electrical wires (e.g., pacemaker leads, polymer based flex cables, or wires) or other types of communications means (e.g., ultrasonic, optical, or electrophysiology signals).

Other aspects and advantages of this invention will be better appreciated from the following detailed description.

BRIEF DESCRIPTION OF THE DRAWINGS

FIG. 4 represents the anchor of FIGS. 1 through 3 in a stowed configuration, and FIG. 5 shows a delivery system in which the anchor of FIGS. 1 through 4 is coupled to a positioning catheter and stowed within a sheath in preparation for an implantation procedure.

DETAILED DESCRIPTION OF THE INVENTION

Figure 1:
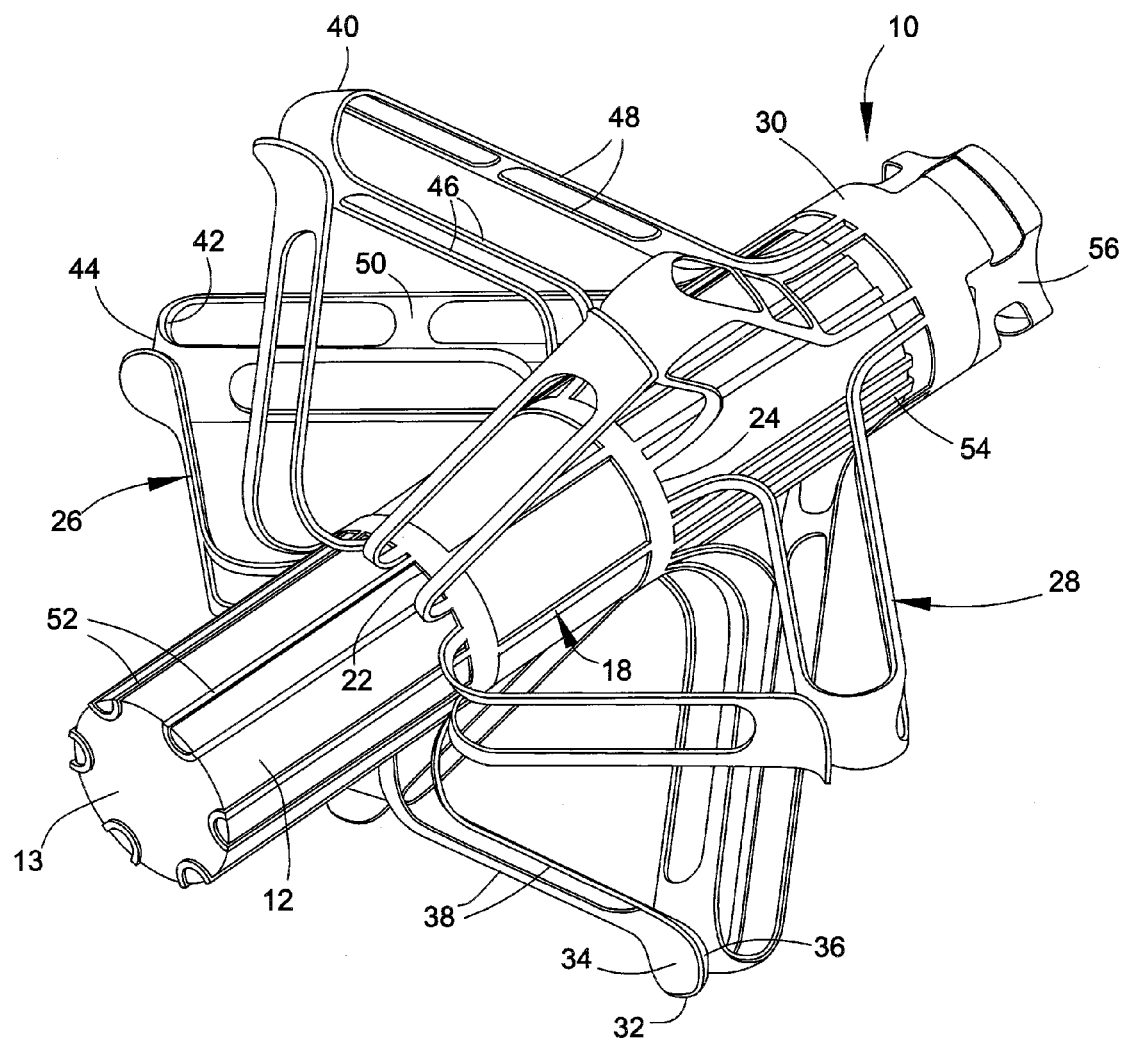
FIG. 1 is a perspective view of an anchor and a medical implant, with the anchor being portrayed in a deployed configuration in accordance with an embodiment of this invention.
Figure 2:
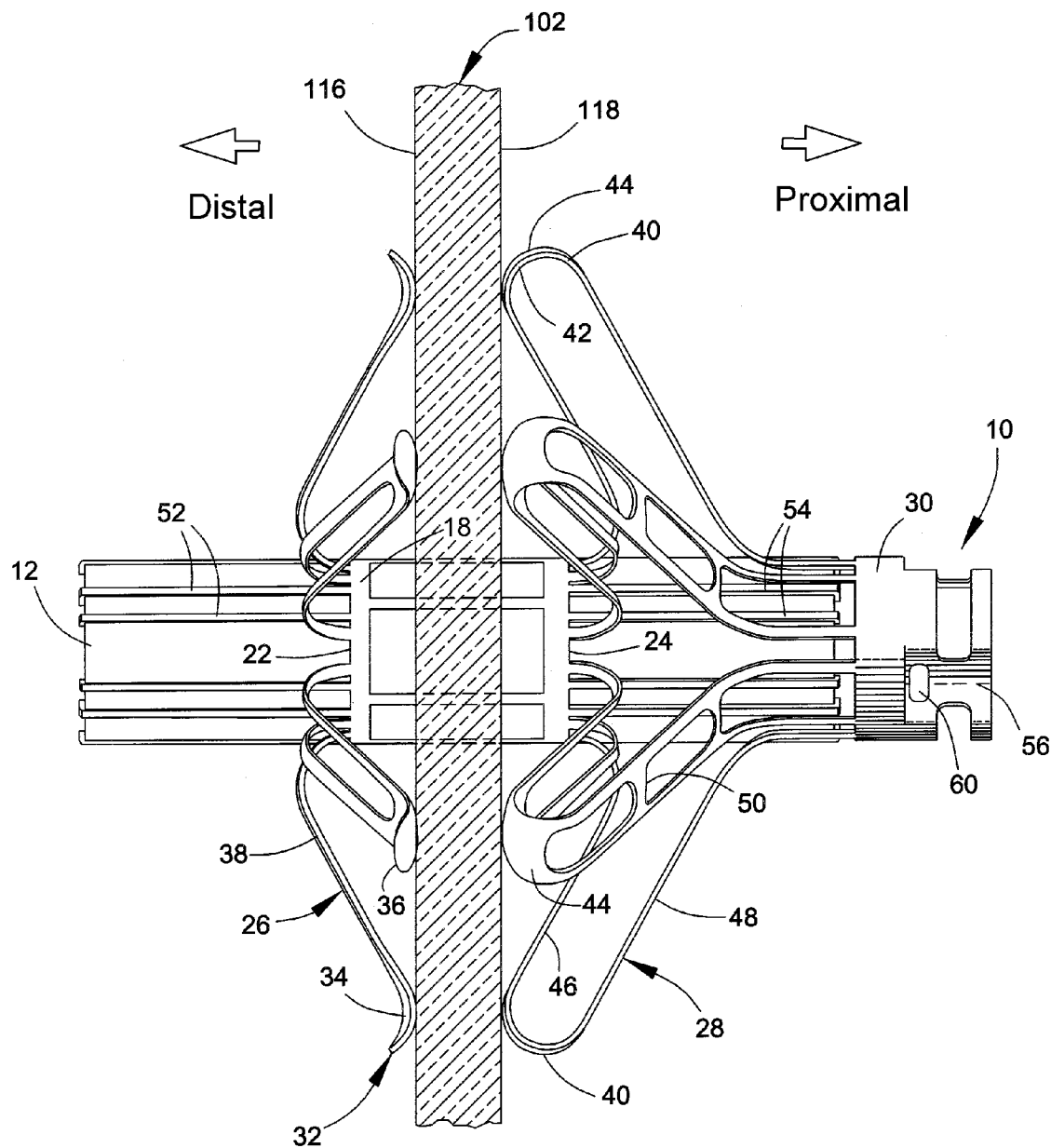
FIG. 2 is a side view of the anchor and implant of FIG. 1 showing the implant anchored to a wall with the anchor as a result of arms and legs of the anchor being deployed on distal and proximal sides, respectively, of the wall
Figure 3:
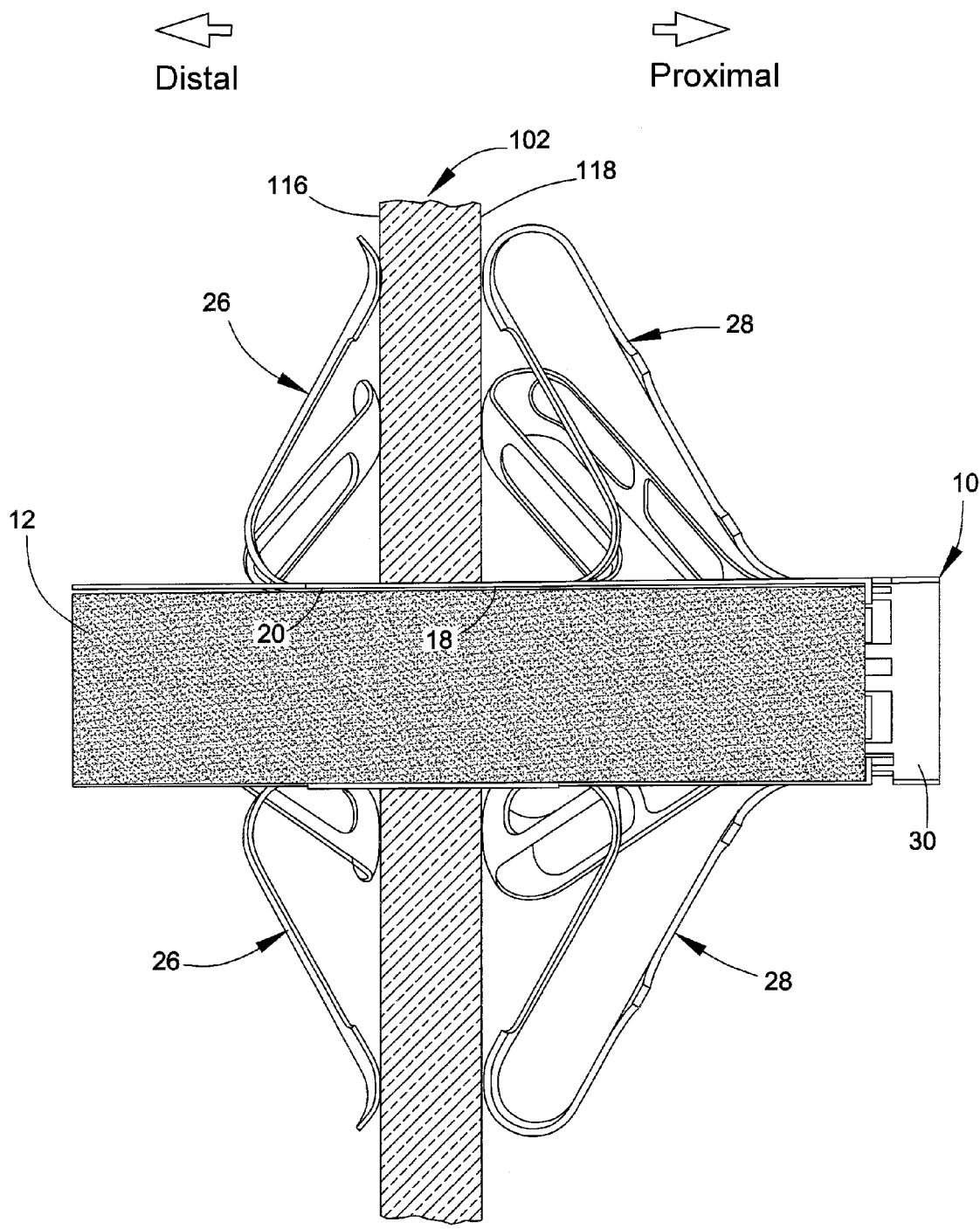
FIG. 3 represents a cross-section through the longitudinal axes of the anchor and implant of FIGS. 1 and 2.

FIGS. 1 through 10 depict an anchor 10 and a delivery system 100 suitable for delivering and securing a medical implant 12 to a wall 102, such as a wall 102 of an internal organ (FIGS. 2 and 3), in accordance with an embodiment of the present invention. As a notable example, the wall 102 can be an atrial septum and the implant 12 can be employed to measure physiological parameters of the heart, such as LVEDP or MLAP. The implant 12 may be any one of a variety of types of implants currently known or developed in the future, and the scope of the present invention is not limited in any way by the type and operation of the implant 12. Implantable devices capable of being delivered with the present invention include but are not limited to wireless implants disclosed in commonly-assigned U.S. Pat. Nos. 6,926,670, 6,968,743, 7,211,048, 7,615,010 and 7,686,762 and U.S. Published Patent Application Nos. 2006/0047205, 2007/0032734, 2008/0077016, 2008/0269573, 2009/0005656, 2009/0105557, 2009/0105784 and 2009/0143696. In the Figures, the implant 12 is represented as having a cylindrical shape, and one of its end surfaces 13 preferably serves as the location of a sensing element, such as a pressure sensing diaphragm. Ideally, the implant 12 is of minimal size, a nonlimiting example being a diameter of about 3.7 millimeters and a length of about 10 millimeters. While a cylindrical implant 12 is shown in FIGS. 1 through 3, the functionality of the anchor 10 is not dependent on any particular shape for the implant 12, and can be readily adapted to secure a variety of different shaped implants with different sensing technologies.

The implant delivery system 100 is represented in FIG. 5 as including the anchor 10 in which the implant 12 is secured, a positioning catheter 14 to which the anchor 10 is coupled, and a sheath 16 in which the catheter 14 and its attached anchor 10 are telescopically received. As such, the anchor 10, catheter 14, and sheath 16 are all generally coaxial. As represented in FIG. 5, the positioning catheter 14 can be hollow to enable fluids to be delivered to or removed from the deployment site of the anchor 10. In addition the hollow catheter 14 also enables the use of a central pusher wire 120, discussed below in reference to FIGS. 9 and 10. The sheath 16 can be of any suitable type known in the art or subsequently developed.

The anchor 10 is depicted in FIGS. 1 through 3 in what will be termed a deployed configuration, meaning the configuration of the anchor 10 when outside the sheath 16 so that portions of the anchor 10 are allowed to deploy, as will be described below. In contrast, FIGS. 4 and 5 depict the anchor 10 in a stowed configuration, meaning the configuration of the anchor 10 while within the sheath 16 (FIG. 5). As such, though FIG. 4 shows the anchor 10 in its stowed configuration for illustrative purposes, the position of the anchor 10 outside the sheath 16 would ordinarily result in the deployed configuration shown in FIGS. 1 through 3.

In FIGS. 1 through 3, the anchor 10 is shown as having an annular-shaped base portion 18 that surrounds the implant 12. The base portion 18 is represented as having a frame-like construction that defines a cage 20 (FIG. 3) in which a portion of the implant 12 is located. The base portion 18 has oppositely-disposed first and second ends 22 and 24 corresponding to oppositely-disposed first and second longitudinal directions parallel to a central axis of the base portion 18, which also defines a longitudinal axis of the anchor 10. For convenience, these directions will be referred to as distal and proximal directions, and various structures of the anchor 10 and system 100, including the ends 22 and 24 of the base portion 18, will be described as being distal or proximal to reflect the orientation of the anchor 10 and system 100 during an implantation procedure described below. However, it should be understood that the invention is not necessarily limited to any particular orientation for the anchor 10.

When stowed (FIGS. 4 and 5), structures of the anchor 10, referred to as arms 26 and legs 28, extend substantially parallel to the axis of the base portion 18 from its distal and proximal ends 22 and 24, respectively. The legs 28 support an annular-shaped coupler member 30, so that the coupler member 30 is axially spaced from the second end 24 of the base portion 18. The arms 26 and legs 28 are resiliently biased so that, when deployed as shown in FIGS. 1 through 3, the arms 26 and legs 28 acquire shapes that preferably lie within angularly spaced radial planes, each containing the axis of the base portion 18. The deployed arms 26 generally deploy by rotating about their respective attachments to the base portion 18 at the distal end 22 thereof, with movement of the arms 26 generally occurring in the proximal direction so that the arms 26 project substantially radially from the longitudinal axis of the anchor 10. When fully deployed, the arms 26 also extend in the proximal direction relative to the distal end 22 of the base portion 18. Each arm 26 terminates with an extremity or distal tip 32, which in the deployed configuration is radially offset from the longitudinal axis of the anchor 10. The distal tip 32 is represented as having a semispherical shape, such that oppositely-disposed concave and convex surfaces 34 and 36 are defined. With the arms 26 in the deployed configuration, the concave surfaces 34 face the distal direction and the convex surfaces 36 face the proximal direction. Each arm 26 is further shown as comprising beams 38, which are generally parallel to each other and spaced apart from each other in directions transverse to the longitudinal axis of the anchor 10. The beams 38 defining spanning portions of the arms 26 that interconnect the distal tips 32 of the arms 26 to the base portion 18. By providing multiple beams 38 within each spanning portion of each arm 26, a level of redundancy is provided in the event one of the beams 38 becomes damaged or breaks.

Each deployed leg 28 generally deploys by rotating about its respective attachment to the base portion 18 at the proximal end 24 thereof, with movement of each leg 28 generally occurring in the distal direction so that the legs 28 project substantially radially from the longitudinal axis of the anchor 10. When fully deployed, the legs 28 also extend in the distal direction (opposite that of the arms 26) relative to the proximal end 24 of the base portion 18. Each leg 28 has an intermediate portion 40, which in the deployed configuration is radially offset from the longitudinal axis of the anchor 10. Similar to the distal tips 32 of the arms 26, each intermediate portion 40 is represented as having a semispherical shape, such that oppositely-disposed concave and convex surfaces 42 and 44 are defined. With the legs 28 in the deployed configuration, the convex surfaces 44 predominantly face the distal direction so as to oppose the distal tips 32 of the arms 26. Each leg 28 is further shown as comprising two sets of beams 46 and 48. One set of beams 46 is disposed between the proximal end 24 of the base portion 18 and the intermediate portion 40, while the second set of beams 48 is disposed between the coupler member 30 and the intermediate portion 40. As with the beams 38 of the arms 26, the leg beams 46 and 48 are generally parallel to each other and the beams 46 and 48 of each set are spaced apart from each other in directions transverse to the longitudinal axis of the anchor 10. The beams 46 and 48 define spanning portions of the legs 28 that interconnect their intermediate portions 40 to the base portion 18 and coupler member 30, respectively. Again, a benefit of this construction is the ability to provide a level of redundancy in the event one of the beams 46 and 48 become damaged or break. The legs 28 further include struts 50 that span the gaps between the individual sets of beams 46 and 48, thereby reinforcing the legs 28 and inhibiting any tendency for the legs 28 to twist during deployment.

As evident from FIGS. 2 and 3, both sets of beams 46 and 48 extend in the distal direction (opposite that of the arms 26) when the legs 28 are fully deployed, such that the intermediate portions 40 of the legs 28 are closer to the distal tips 32 of the arms 26 than the beams 46 and 48 of the legs 28. With the arms 26 and legs 28 in their deployed configurations, the convex surfaces 36 and 44 of the arms 26 and legs 28 are axially aligned with each other, providing a clamping capability on the wall 102 as evident from FIGS. 2 and 3. For this reason, each arm 26 is preferably paired with one of the legs 28, such that each paired set of arms 26 and legs 28 lies in the same radial plane when the anchor 10 is deployed, and each paired set of arms 26 and legs leg 28 is collinear when the anchor 10 is stowed. The deployment of the arms 26 and legs 28 toward each other enables the anchor 10 to accommodate walls (102) of different and varying thicknesses. While the diameters defined by the deployed arms 26 and legs 28 can be adapted for the particular intended application, examples of suitable diameters may be in a range of about 13.5 to 15 millimeters, with the legs 28 preferably defining a larger diameter than the arms 26.

FIGS. 1 through 4 further show the anchor 10 as having flexible retention fingers 52 and 54 that extend in the distal and proximal directions from the distal and proximal ends 22 and 24, respectively, of the base portion 18. Similar to the arms 26 and legs 28 of the anchor 10, each retention finger 52 and 54 comprises spaced-apart beams that are generally parallel and spaced apart from each other in directions transverse to the longitudinal axis of the anchor 10. The tip of each retention finger 52 and 54 extends radially inward toward the longitudinal axis of the anchor 10. As evident from FIGS. 1 through 3, the retention fingers 52 and 54 effectively define extensions of the cage 20 defined by the base portion 18, with opposite ends of the implant 12 abutting the tips of the retention fingers 52 and 54. The implant 12 can be placed within the cage 20 be deflecting either set of retention fingers 52 and 54 radially outward to create an opening large enough to accommodate the diameter of the implant 12, such that a spring load positively retains the implant 12 within the cage 20 so that pulsation effects of the heart or blood flow do not cause movement of the implant 12 that might lead to potentially false signal data. Movement of the implant 12 is also inhibited as a result of the balanced weight distribution that can be achieved with the anchor 10, and in particular the central location of the cage 20 relative to the deployed positions of the arms 26 and legs 28, as evident from FIG. 3.

Though the flexible retention fingers 52 and 54 are preferred for retaining the implant 12, it should be appreciated that retention of the implant 12 in the anchor 10 can be accomplished in different ways. For example, one or any combination of the following securement techniques could be used: cam slots, threads, snaps, snap latches, latch fingers, spring latches, latch fingers with a catheter sheet on top to release the latch, one or more guidewires or catheters to either latch or release coupling means (such as latching fingers), dissolvable glues, temporary glues, thermal glues, heated shape memory latches, unheated shape memory latches, heated mechanical means, piezoelectric release system, hydraulic coupling systems, pneumatic coupling systems, magnetic coupling systems, etc.

Figure 7:
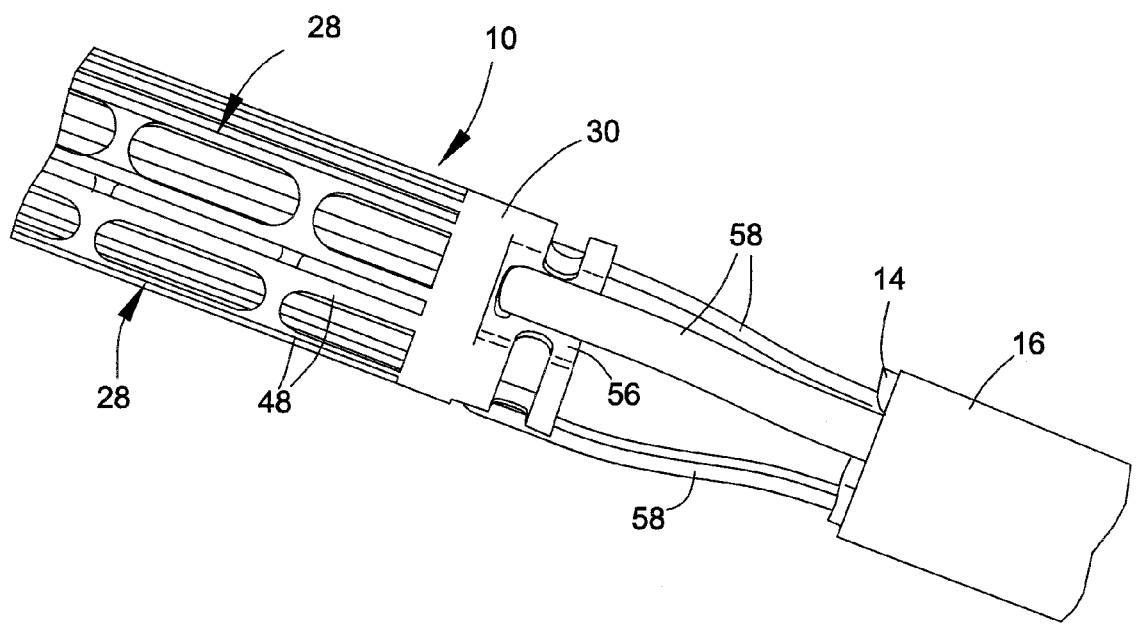
FIG. 7 is a side view showing the anchor of FIGS. 1 through 6 coupled to the positioning catheter in accordance with a preferred embodiment of the invention.

The coupler member 30 is configured for coupling with the positioning catheter 14, as shown in FIGS. 5 and 7. The coupler member 30 has an annular shape that, along with the catheter 14 and the remainder of the anchor 10, can be accommodated within the sheath 16. As best seen in FIG. 7, the coupler member 30 is formed to have channels, troughs or slots 56 corresponding in number to the number of connectors, referred to herein as link fingers 58, which project from the distal end of the catheter 14. A window 60 (or other suitable recessed feature) is defined within each slot 56 that can be engaged by a distal tip of each link finger 58. By using the sheath 16 to hold the distal tip of each link finger 58 in its respective window 60, as is the case when the positioning catheter 14 and anchor 10 are disposed within the sheath 16 (FIG. 5), the anchor 10 is secured to the catheter 14 with the link fingers 58, but can be quickly released by moving the catheter 14 relative to the sheath 16 to expose the link fingers 58, which are formed to be elastically biased radially outward so that the fingers 58 expand when released by the sheath 16 and their distal tips disengage from their windows 60.

Another feature of the coupling scheme represented in the Figures is that the coupler member 30 and the link fingers 58 do not form a rigid joint, but instead create an articulating joint in that the anchor 10 has some freedom of movement in directions transverse to the axis of the catheter 14. Specifically, by causing the link fingers 58 to move relative to each other, the anchor 10 is articulated relative to the catheter 14, which facilitates threading the anchor 10 through a patient's arterial system.

According to a preferred aspect of the invention, the entire anchor 10 can be fabricated as a unitary body, and therefore without resorting to any assembly techniques involving metallurgical joining (e.g., welding, brazing, etc), mechanical joining (e.g., fasteners, threads, latches, deformation, etc.), or bonding (e.g., adhesive), though such assembly methods could be used and are therefore within the scope of the invention. As such, the entire anchor 10 can be fabricated from a single preform, such as by cutting a tubular-shaped preform to form the base portion 18, arms 26, legs 28, coupler member 30, and retention fingers 52 and 54, and then deforming the arms 26, legs 28, coupler member 30, and retention fingers 52 and 54 as required to acquire the deployed shape of the anchor 10 shown in FIGS. 1 through 3.

Many existing medical implantable devices for use in the heart utilize NITINOL®, a "shape-memory" nickel-titanium alloy that enables an umbrella-like structure folded inside a catheter for delivery to later automatically expand once outside the catheter for implantation. In a preferred embodiment, the anchor 10 is formed of NITINOL® or another suitable shape-memory material. According to another preferred aspect, the anchor 10 can be manufactured primarily by laser cutting techniques performed on solid tubes of a shape memory material, rather than primarily using welding techniques as typically done in the prior art. Fabrication of the anchor 10 using laser cutting techniques provides at least two advantages. First, the reliability of the anchor 10 is much higher since its components (base portion 18, arms 26, legs 28, coupler member 30, and retention fingers 52 and 54) are integral portions of a single metal piece. Welded joints possess higher risk of failure than that possible with the preferred unitary construction for the anchor 10. Secondly, the cost of manufacturing can be significantly lower than would be possible if relying primarily on welding to form the anchor 10.

In practice, a NITINOL® tube can be cut by laser alone to form an anchor preform. The laser cutting operation can be performed as an automated process based on drawing files using commercial mechanical design software. The tubular-shaped anchor preform is then formed to the extent necessary to obtain the desired 3-D shape for the stowed configuration of the anchor 10 shown in FIGS. 4 and 5. Thereafter, the desired 3-D shape for the deployed configuration (FIGS. 1 through 3) can be produced by further forming the anchor 10, after which the shape memory effect is achieved by placing the anchor 10 in a mechanical jig and heating the anchor 10 to an appropriate temperature to store the shape into the memory of the NITINOL® material. After its fabrication, the anchor 10 preferably undergoes chemical passivation in order to reduce the corrosion tendencies of NITINOL® in body fluids, and then coated with a suitable biocompatible coating such as parylene C. Prior to being coated, the anchor 10 can be subjected to electro-polishing or another suitable treatment that smoothes corners and edges of the anchor 10, such that stresses are reduced and adhesion of the coating is promoted. Prior to placement in the anchor cage 20, the implant 12 can also be coated with parylene C or another suitable biocompatible coating.

A key parameter of any wireless, implantable system is the communication distance (both tele-powering and tele-communication) between the implant 12 and a remote readout handheld unit (not shown). Since the anchor 10 may be formed of a metal such as NITINOL®, there exists a potential that such a metallic anchor could adversely affect (reduce) the communication distance between the implant 12 and the handheld unit by acting similar to a Faraday cage. Tests performed using metal implants indicated that telemetry communication distances can be reduced by about two-thirds, such that placing an implant using RF/electromagnetic telemetry inside a metal anchor would not be expected to achieve reasonable performance. To overcome this problem, the anchor 10 is configured to avoid the primary causes of reduced communication distances.

Attenuation was determined to depend on parameters including the number of metal loops formed by the anchor, the orientation of the loops, and whether the loops are arranged in such a manner as to form a mesh or cage. Fewer numbers of metal loops were associated with longer communication distances. Furthermore, metal loops that are arranged in parallel to the implant communication coil (with or without a ferrite core) were found to not adversely affect the communication distance, while metal wires oriented perpendicular to the implant communication coil (with or without a ferrite core) were found to greatly reduce such magnetic fields. The anchor 10 of the present invention comprises two loops (the base portion 18) that surround the implant 12. In the embodiment shown in FIGS. 1 through 3, the anchor 10 makes satisfactory use of only six arms 26 and six legs 28. Furthermore, from FIGS. 1 through 5 it can be appreciated that the size of the cage 20 enclosing the implant 12 and each element (base portion 18 and retention fingers 52 and 54) forming the cage 20 is minimized and their locations selected so that signals (e.g., data transmission and/or powering) received and transmitted by the implant 12 suffer minimal attenuation. As such, the configuration of the anchor 10 minimizes metal shielding effects, which is beneficial if the implant 12 is wirelessly operated, such as by radio frequency (RF) telemetry, and renders the anchor 10 of this invention practical for use with small implants across long communication distances. The low-profile configuration of the anchor 10 also minimizes the diameter required of the sheath 16 used to delivery the anchor 10 and implant 12, and advantageously results in the anchor 10 exerting minimal stress on the implant 12.

The anchor 10 may be employed to place the implant 12 in various locations, depending on the physiological parameter of interest. For the purpose of diagnosing, monitoring, and/or treating a cardiovascular diseases such as congestive heart failure (CHF), valvular heart disease, systemic pulmonary hypertension, or congenital heart disease (CHD), LVEDP and/or MLAP are of most importance, and therefore the left chambers of the heart or immediately attaching vessels are among preferred locations for the implant 12. Because the number of implants is not practically limited by the technology, multiple locations for blood pressure measurement are easily established, including all chambers of the heart, major arteries and appendages. The preferred waveforms to monitor for congestive heart failure applications are the pressures of the left atrium. The monitored waveforms may include, but are not limited to, a complete detailed LA waveform, particularly an accurate MLAP, that is continuous and in real time. It should be mentioned that some aspects of the anchor 10 described above will allow pressure measurements of the right atrium (by locating the pressure sensor at the end of the implant 12 facing the right atrium) or both right and left atriums (for example, using two pressure sensors, one at each end of the implant 12), or direct differential pressure measurement between the right and left atrium (again, for example, using two pressure sensors, one at each end of the implant 12). In addition to or instead of pressure, other parameters can easily be monitored using an implant delivered and placed with the anchor 10. Such parameters include but are not limited to temperature, blood chemistry, oxygen level, etc. For example, a hydrogel film (with selectivity to different elements) can be placed on top of a pressure sensor to measure the presence of elements that cause the hydrogel to expand, thereby applying pressure to the pressure sensor.

Thrombogenicity is the primary concern when considering a device for implantation in the left side of the heart, due to the possibility of thrombi reaching the brain. In order to assure such high-level of nonthrombogenicity, the present invention seeks to reduce such risks through proper anchor shape, anchor location, and delivery method. Thrombogenesis can be caused by direct chemical interaction with an implant or anchor, and by blood flow turbulence resulting from implant geometry. Regarding the former, the above-noted materials for the anchor 10 are selected to be either biocompatible or covered by biocompatible materials. As to the latter, the anchor 10, implant 12 and their previously-noted dimensions provide for a hydrodynamic sensor profile that minimizes the protrusion of the anchor 10 and implant 12 outside the wall 12 which, combined with the ability of the anchor 10 to achieve a balanced weight distribution for the implant 12 within the wall 102, minimize the blood flow turbulence caused by the implant 12 and anchor 10 within the blood flow path whose parameters are being sensed. As previously noted, a preferred location for the sensing element (such as a pressure sensing diaphragm) is believed to be on the flat end surface 13 of the cylindrical implant 12 facing the distal direction of the anchor 10, so that only a small portion of the implant 12 is required to protrude beyond the wall 103. However, it is also within the scope of the invention to place the sensing element of the implant 12 near the end 13 of the implant 12. Subsequent cell growth over the exposed end 13 of the implant 12 will further reduce the risk of thrombogenicity. For sensing parameters in the left atrium, the implant 12 can be preferably placed with the anchor 10 at two desirable locations: the atrial septum and left atrial appendage. The atrial septum is believed to be preferable for locating the anchored implant 12.

If placed in the atrial appendage, the implant 12 may be anchored by expanding the anchor 10 and then occluding the appendage with the implant 12. In this case, thrombi formation on the distal end of the implant 12 would not pose a risk to the patient, as evidenced by previous left atrial appendage devices that have been introduced for this very purpose.

A reason for preferring placement in the atrial septum is that there exists FDA-approved, commercially-available medical devices for chronic implantation in this location. These devices, for example, are used to occlude atrial septum defects and other vascular holes. The implant 12 can be anchored to the atrial septum with similar techniques as FDA-approved, commercially-available devices such as the AMPLATZER® family of devices commercially available from AGA Medical, or the CardioSEAL commercially available from NMT Medical. These devices have been shown to be suitable for cardiovascular implantation. As a result, one may take advantage of this existing infrastructure, including standard practices of delivering cardiovascular implants. Another advantage of placing the implant 12 within the wall 102 of the atrial septum is that the potential adverse confounding effects of the muscle contraction on the sampled pressure measurements will be considerably reduced.

Delivery of the implant 12 with the anchor 10 demands such considerations as safety, minimal invasiveness, suitability as an outpatient procedure, ease of operation, preferable use of existing practices, minimum training for the physician/technician, and the ability to allow multiple tries before deploying and releasing the anchor 10. As discussed above, the preferred delivery method for the anchor 10 is believed to be by catheter delivery, discussed below in more detail. To minimize catheter diameter, the implant 12 is preferably small and thin. Delivery and placement of the anchor 10 is able to make use of standard current practices in the cardiovascular field to reduce both time and cost of R&D and manufacturing, create comfort and confidence in cardiologists, and make FDA process easier. The anchor 10 is configured so that, after it is coupled to the link fingers 58 of the positioning catheter 14 and placed in the sheath 16, the diameter of the stowed anchor 10 is equal or as close as possible to the diameter of the original tube from which the anchor 10 was laser cut. This approach renders the smallest possible diameter of the catheter 14 and sheath 16, for example, a sheath diameter of about 4.7 millimeters (French 14).

Figure 8:
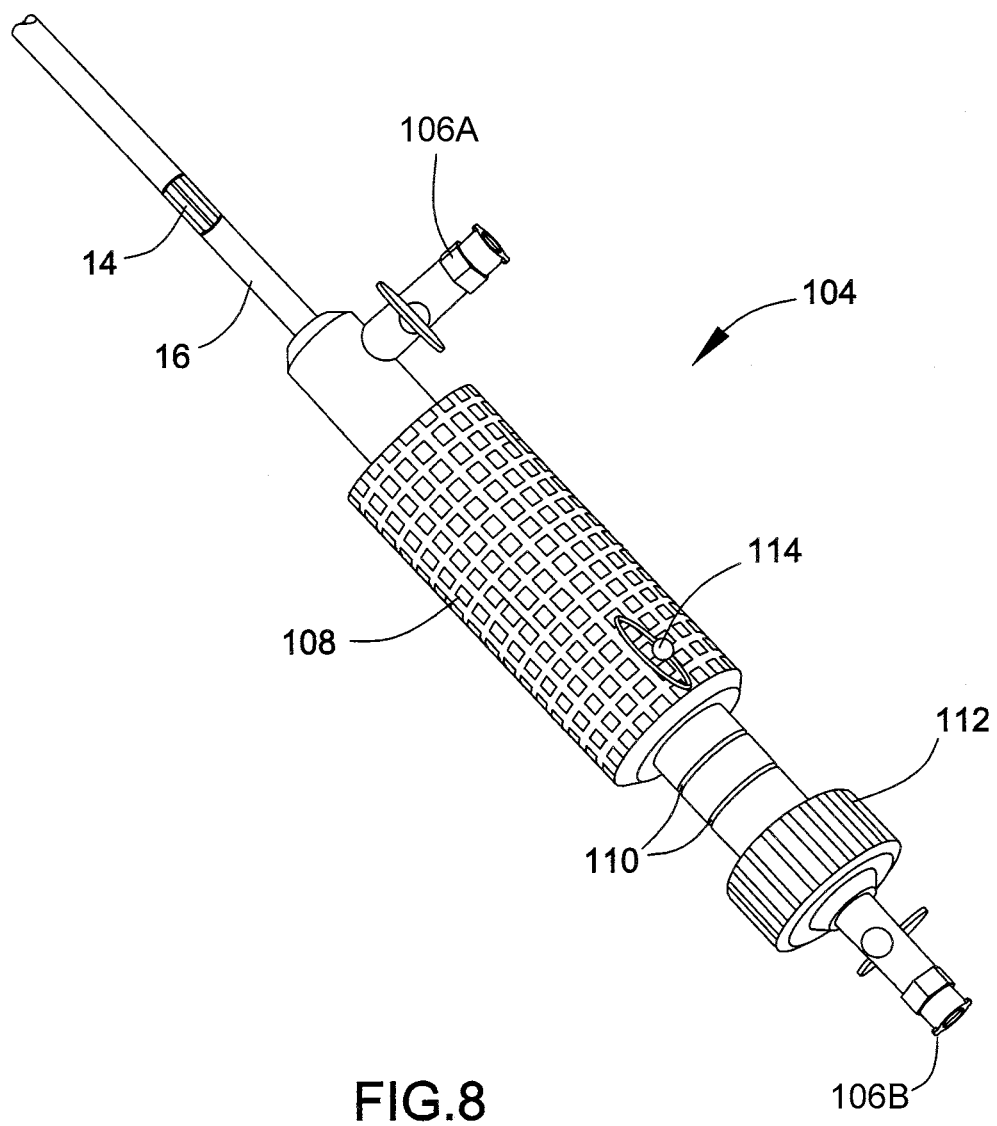
FIG. 8 is a perspective view representing a handle assembly adapted for use with the delivery system of FIGS. 5 and 6.

FIG. 8 represents a particularly suitable handle assembly (manipulator) 104 for use with the delivery system 100. The handle assembly 104 includes flushing ports 106A and 106B and valves that allow the introduction of a flushing fluid into the catheter 14 and/or sheath 16 and the removal of the flushing fluid during the implantation procedure. The ports 106A and 106B and their valves also allow air to be flushed that could lead to an embolism. The handle assembly 104 further includes a grip 108, deployment range and position markers 110, a catheter tip steering control knob 112, and a safety retainer 114. The grip 108 is part of a slide mechanism that controls the longitudinal movement of the positioning catheter 14 relative to the sheath 16. The markers 110 assist the operator in determining the position of the distal tip of the catheter 14 relative to the distal tip of the sheath 16. The steering control knob 112 operates a catheter tip steering mechanism (not shown). As known in the art, such a mechanism employs wires (not shown) within the positioning catheter 14 that cause the distal tip of the catheter 14 to curl when they are appropriately pulled, which in turn results in articulation of the anchor 10 mounted to the distal tip of the catheter 14. Finally, the safety retainer pin 114 limits the movement of the grip 108 until such time as is deemed appropriate for releasing the anchor 10 from the catheter 14.

The two flushing ports 106A and 106B are connected to "dead spaces" within the sheath 16, identified in FIG. 5. The port 106A located on the side of the handle 108 is connected to a dead space 128 between the outer surface of the catheter 14 and the inner surface of the sheath 16, and the port 106B located at the end 126 of the handle 108 is connected to a dead space 130 defined by the internal lumen of the catheter 14. As evident from FIG. 5, the dead spaces 128 and 130 fluidically communicate in proximity of the link fingers 58. A positive pressure flush can be connected to, for example, the port 106A, to allow for filling the increasingly large dead space 128 with saline as the anchor 10 is advanced through the sheath 16, thereby avoiding the creation of a negative pressure within both dead spaces 128 and 130. The continuously flowing saline is then discharged through the port 106B. By using a positive flush through the port 106A, the dead spaces 128 and 130 are continuously full of fluid that is continuously flushed as the anchor 10 is moved towards the heart, while avoiding exposure of the patient to a volume overload of the flushing fluid and also reducing the risk of air-emboli and thrombo-emboli.

Figure 6:
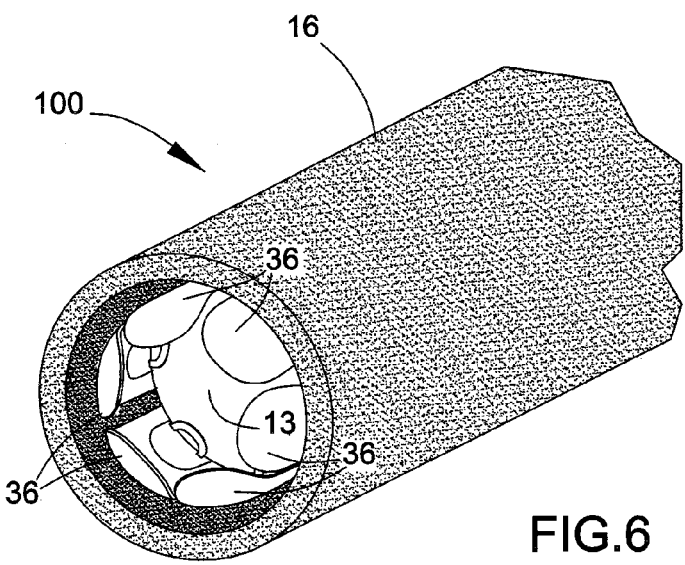
FIG. 6 is a perspective view showing a distal tip of the sheath of FIG. 5.

Using a standard cardiology guidewire via a standard procedure (not shown), the handle assembly 104 can be used to pass the sheath 16 through a patient's arterial system and place the sheath 16 through an opening in the atrial septum 102, for example, a puncture created by a standard transsptal procedure. The catheter 14 with its anchor 10 and implant 12 are then passed through the sheath 16 until located within the distal end of the sheath 16, as represented in FIGS. 5 and 6. The handle assembly 104 is then operated to extend the catheter 14 relative to the sheath 16 to the extent that the arms 26 of the anchor 10 are released from the sheath 16 and the shape-memory property of the anchor material causes the arms 26 to deploy within the left atrium. As evident from FIG. 5, the convex surfaces 36 of the distal tips 32 of the arms 26 project radially inward over the end surface 13 of the implant 12 where the sensing element (such as a pressure sensing diaphragm) is preferably located. In this manner, the distal tips 32 are advantageously capable of protecting the surface 13 and its sensing element from damage as the anchor 10 and implant 12 are simultaneously extended from the distal end of the sheath 16. The convex surfaces 36 of the tips 32 also act to reduce the force required to insert the anchor 10 through the septum wall 102, enhance the ability of the anchor 10 to navigate blood vessel curvatures, and reduce the likelihood that the anchor 10 will damage blood vessel walls.

As previously noted, the arms 26 deploy in the proximal direction toward the distal surface 116 of the septum wall 102. The handle assembly 104 can then by withdrawn slightly to simultaneously retract the sheath 16 and catheter 14 into the right atrium, causing the deployed arms 26 to bear against the septum wall 102. The sheath 16 can then be further retracted to expose the entire lengths of the legs 28, resulting in the legs 28 deploying to the configuration represented in FIGS. 1 through 3. As with the arms 26, deployment of the legs 28 results from the shape-memory property of the anchor material, which causes the intermediate portions 40 of the legs 28 to move radially outward and in the distal direction to engage the proximal surface 118 of the septum wall 102.

Up to this point, the entire procedure can be reversed, so that the anchor 10 and its implant 12 can be repositioned or even entirely withdrawn from the body. The safety retainer pin 114 of the handle assembly 104 is adapted to prevent an accidental release of the anchor 10 from the catheter 14. At the proper time, the medical personnel operating the handle system 104 to implant the anchor 10 can use an imaging system (not shown) to verify that the anchor 10 is in the desired position relative to the septum wall 102. Notably, the steering control knob 112 can be used to operate the catheter tip steering mechanism, by which rotation of the knob 112 causes the distal tip of the positioning catheter 14 to curl. This motion, along with the ability to rotate the entire sheath 16, allows the anchor 10 to be articulated relative to the sheath 16 to achieve proper alignment and placement of the anchor 10. If the medical personnel are satisfied with the deployment and location of the anchor 10, the safety retainer pin 114 can be removed to allow further movement of the grip 108 (slide mechanism) that will result in the positioning catheter 14 being sufficiently moved to cause the anchor 10 to be decoupled from the catheter 14 as a result of the catheter link fingers 58 disengaging the windows 60 in the coupler member 30 of the anchor 10. In preferred embodiments, the insertion and deployment operations performed with the handle system 104 intentionally require the use of both hands of the person performing the implantation procedure, such that a second person is needed to remove the safety retainer pin 114 and release the anchor 10. The deployment range and position markers 110 on the handle assembly 104 can be used as visual indications of the status of the anchor deployment in the event that an imaging system is unavailable, or fails, or otherwise becomes ineffective. The positions of the markers 110 can be matched to detents in the slide mechanism that provide an additional tactile signal of the position of the catheter 14 within the sheath 16.

After the link fingers 58 are disengaged from the windows 60 in the coupler member 30 to uncouple the anchor 10 from the catheter 14, the catheter 14 can be retracted into the sheath 16 and the catheter 14 and sheath 16 can be withdrawn together, leaving the anchor 10 and its implant 12 secured within the septum wall 102, as depicted in FIGS. 2 and 3. Even after the anchor 10 is released from the catheter 14, it is still possible to recapture the anchor 10 by forcing the link fingers 58 into the slots 56 of the coupler member 30 to re-engage the windows 60 and permit the anchor 10 to be retracted back into the sheath 16.

Figure 9:
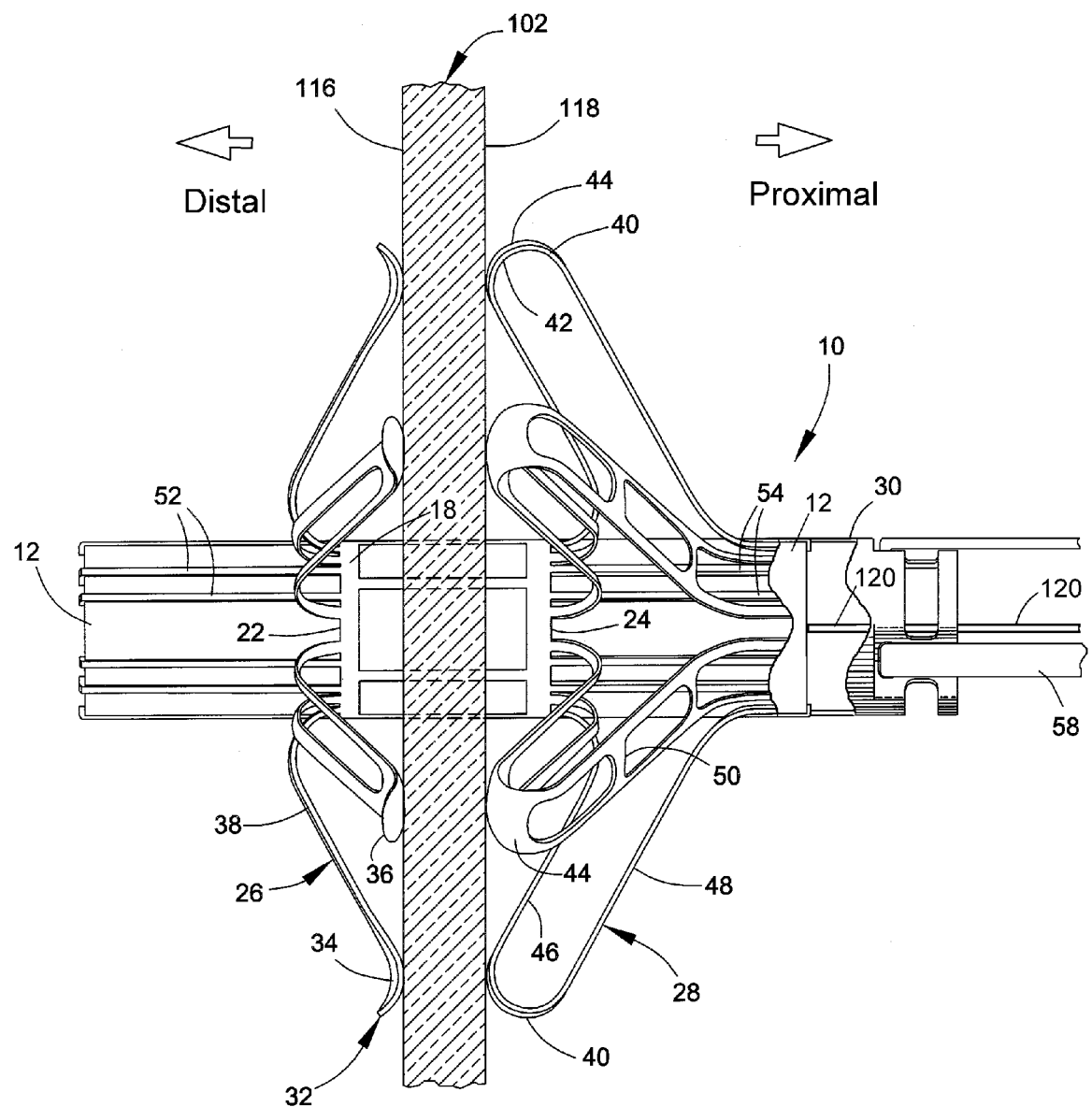
FIG. 9 is a side view of the anchor and implant similar to that of FIG. 2, but further showing a partial cross-section of the anchor and the use of a central pusher to fully re-collapse the proximal legs of the anchor in the event that the anchor needs to be repositioned or retrieved from the wall.
Figure 10:
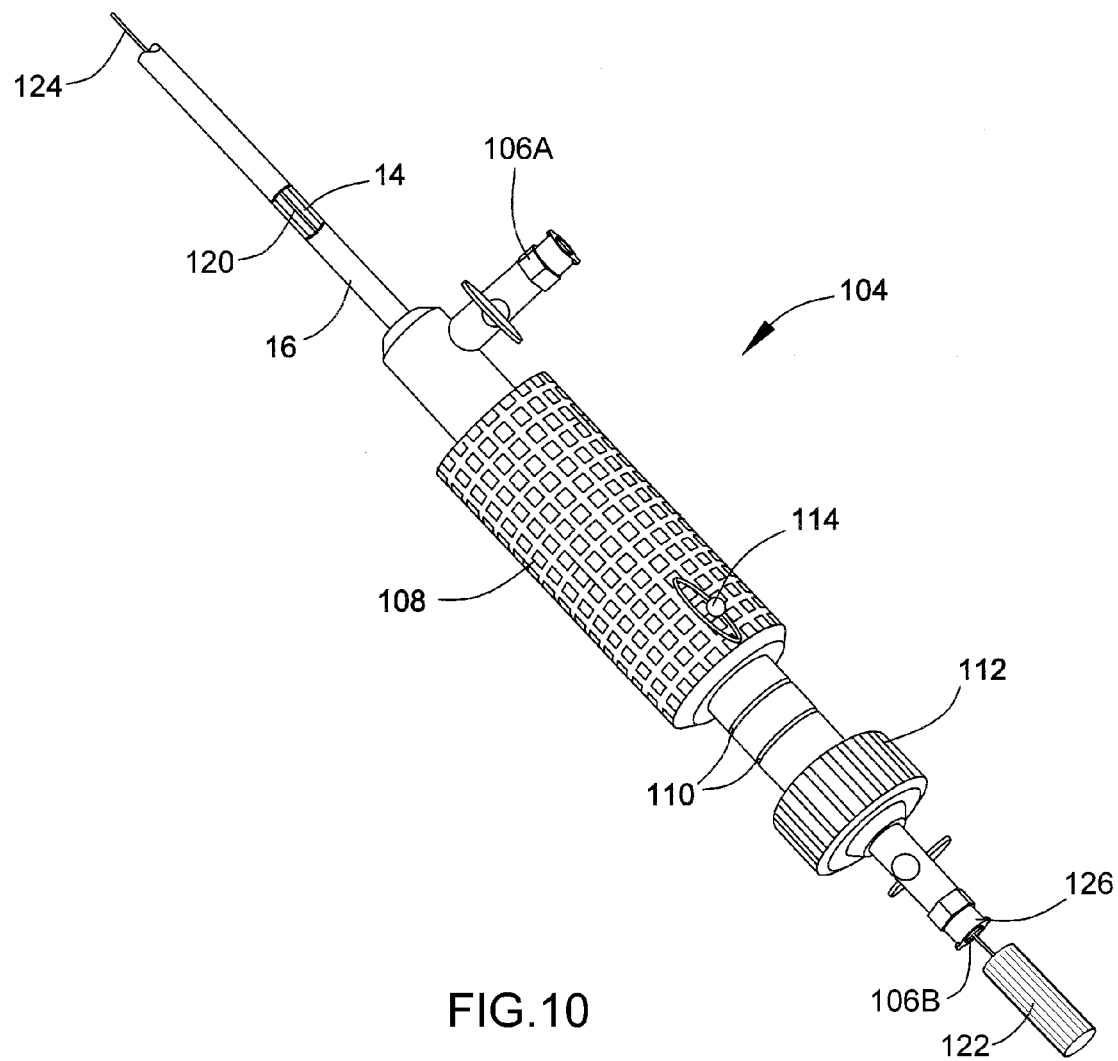
FIG. 10 is a perspective view representing the handle assembly of FIG. 8 further equipped with the central pusher of FIG. 9.

FIGS. 9 and 10 represent an additional aspect of the invention that facilitates repositioning and even retrieval of the anchor 10 and its implant 12 from the septum wall 102 after its deployment. This aspect of the invention makes use of the previously-noted central pusher wire 120, which is passed through the hollow catheter 14 and used to apply a back force on the implant 12 (in the distal direction) while an opposing force is applied by the link fingers 58 to pull the anchor 10 back into the sheath 16 (in the proximal direction). In this manner, the anchor 10 can be effectively stretched so that its legs 28 require their pre-deployed configuration, allowing the anchor 10 and implant 12 to be completely pulled back into the sheath 16. This feature of the invention results in the anchor 10 being fully retrievable and reusable in the same patient during the same procedure, without the need for extracting the implant 12 from the delivery system 100 before attempting another placement.

For the purpose of applying the desired back force, the pusher wire 120 is preferably formed of a stiff material, for example, a stiff guide wire. In particular, the distal end 124 of the pusher wire 120 is sufficiently stiff so that it does not buckle when deployed outside the catheter 14 and used to apply the back force to the implant 12, as represented in FIG. 9. Commercial examples of stiff guidewires include those available under the AMPLATZER® name, including No. 9-GW-001, which is listed as having a diameter of 0.035 inch (about 1.27 mm). The pusher wire 120 is also preferably equipped with a handle 122, as represented in FIG. 10. In addition to simplifying the handling of the pusher wire 120, the handle 122 can also serve to define the maximal distance the pusher wire 120 can be introduced into the catheter 14. In particular, the length of the pusher wire 120 is preferably such that the distal end 124 of the pusher wire 120 stretches the legs 28 to their pre-deployed length when the pusher wire 120 is moved to its most distal position relative to the handle assembly 104 so that the pusher handle 122 contacts the delivery sheath end 126 of the handle assembly 104. This limitation of the movement of the pusher wire 120 avoids the risk of excessive force being applied to the implant 12, which could dislodge the implant 12 from the anchor 10 and lead to the risk of implant embolization. To provide this safety feature, the length of the pusher wire 120 (the distance between its distal end 124 and handle 122) is shorter than standard guidewires used for a given catheter length, for example, the aforementioned AMPLATZER® No. 9-GW-001, which is listed as having a length of 260 cm.

The combination of a catheter 14 having a steerable distal tip (discussed above) and two flush ports 106A and 106B further provides for a safer de-airing procedure in comparison to traditional systems. In order to place the anchor 10 in the left atrium with the steerable distal tip of the catheter 14, the proximal end (closest to the operator) of the sheath 16 is normally passed downward through the groin and the femoral and iliac veins into the vena cava inferior. Within the vena cava inferior and close to its connection with the right atrium, the sheath 16 starts on an upward path into the atrial septum and left atrium. If the distal end of the sheath 16 is higher than the central portion of the sheath 16, there is a risk that during de-airing (flushing the system with saline) any air bubbles within the distal portion of the catheter 14 may travel into the left atrium instead of being aspirated during flushing. The steerable distal tip of the catheter 14 enables the tip of the catheter 14 to be actively lowered during flushing to avoid a geometry that could lead to air bubbles traveling into the left atrium. The continuous flushing effect enabled by the two flushing ports 106A and 106B further promotes the ability to flush air bubbles out of the body.

As previously noted, the anchor 10 can be manufactured to minimize its stowed diameter, permitting the use of small diameter catheters 14 and sheaths 16. On the other hand, the use of a large bore catheter 14 having a steerable distal tip allows for safe immediate placement over a trans-septal needle/dilator set, in other words, without the need for exchange guide-wire use after trans-septal puncture and sheath placement. In addition to eliminating one or more steps, this aspect of the invention can further reduce the risk of air-embolism and thrombo-embolism.

In addition to the delivery and anchoring of wireless implanted medical devices, the anchor 10 and delivery method of this invention can be utilized for non-wireless applications. For example, a pressure sensor (or any other type of sensor) located in the left atrium (or elsewhere) can be provided with a communication connection to other medical devices (such as, but not limited to, pacemakers) from the right atrium side of the anchor/implant. Potential communication connections include, but are not limited to, electrical wires, pacemaker leads, flexible cables, optical connectors, ultrasonic pads, and electrophysiology signals. Hermetic electrical connection pads (instead of or in addition to a pressure sensor) can be provided from inside the implant 12 to its exterior. Such pads can be used to provide electrical connections to other medical devices, e.g., pacemakers, or provide electrical connections to other sensors (e.g., blood chemical sensors), which are made independently of implant 12 and anchor 10. Preferred locations for these pads are believed to be either of the flat ends of the cylindrical implant 12 shown in the Figures, for locating the pads in the left side, right side, or both sides of the heart.

While the invention has been described in terms of preferred embodiments, it is apparent that other forms could be adopted by one skilled in the art. Therefore, the scope of the invention is to be limited only by the following claims.

The invention claimed is:

1. A delivery system comprising a hollow catheter, an anchor coupled to the catheter, and an implant secured within the anchor, the anchor having stowed and deployed configurations and comprising:
    a base portion having a longitudinal axis and comprising first and second longitudinal ends in oppositely-disposed first and second longitudinal directions, respectively, of the anchor, and a cage between the first and second longitudinal ends, the medical implant being secured within the cage of the base portion so that at least a portion of the implant is between the first and second longitudinal ends of the base portion;
    a coupler portion releasably coupled to the catheter and connected to and spaced apart from the second longitudinal end of the base portion in the second longitudinal direction of the anchor, wherein longitudinal concave troughs are defined in the coupler portion and each of the longitudinal concave troughs has a recess therein and is contiguous with an end of the coupler portion farthest from the base portion;
    a plurality of flexible arms and legs that, in the stowed configuration of the anchor, axially extend from the first and second longitudinal ends, respectively, of the base portion, the arms and legs being resiliently biased so that, in the deployed configuration of the anchor, the arms radially project away from the longitudinal axis of the base portion and axially project toward the second longitudinal end of the base portion and the legs project radially away from the longitudinal axis of the base portion and axially project toward the first longitudinal end of the base portion; and means for articulating movement of the anchor relative to the catheter in directions transverse to the longitudinal axis of the base portion, the articulating means including at least three connectors that project from the catheter and engage the coupler portion and means for causing the at least three connectors to move relative to each other and thereby cause articulation of the anchor relative to the catheter in directions transverse to the longitudinal axis of the base portion, wherein the at least three connectors are received in the longitudinal concave troughs of the coupler portion and distal tips of each of the at least three connectors engage the recesses in the longitudinal concave troughs such that the distal tips of the at least three connectors are radially confined within a radial profile of the coupler portion.

2. The delivery system according to claim 1, wherein the connectors of the catheter are operable to decouple from the coupler portion by moving in radially outward directions from the coupler portion to disengage the recesses of the longitudinal concave troughs.

3. The delivery system according to claim 1, wherein the connectors of the catheter are operable to couple with the coupler portion by moving in radially inward directions towards the coupler portion to engage the recesses of the longitudinal concave troughs.

4. The delivery system according to claim 3, wherein radially inward surfaces of the connectors are in direct contact with the longitudinal concave troughs when the connectors are coupled with the coupler portion.

5. The delivery system according to claim 1, wherein the distal tips of each of the at least three connectors comprise protrusions extending in radially inward directions towards the coupler portion, the protrusions engaging the recesses in the longitudinal concave troughs when the connectors are coupled with the coupler portion.

* * * * *